US008604431B2

United States Patent
Murakawa et al.

(10) Patent No.: US 8,604,431 B2
(45) Date of Patent: Dec. 10, 2013

(54) PATTERN-HEIGHT MEASURING APPARATUS AND PATTERN-HEIGHT MEASURING METHOD

(75) Inventors: Tsutomu Murakawa, Tokyo (JP); Hidemitsu Hakii, Tokyo (JP); Isao Yonekura, Tokyo (JP)

(73) Assignees: Advantest Corp., Tokyo (JP); Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 13/407,521

(22) Filed: Feb. 28, 2012

(65) Prior Publication Data

US 2012/0217392 A1    Aug. 30, 2012

(30) Foreign Application Priority Data

Feb. 28, 2011  (JP) .................................. 2011-041674

(51) Int. Cl.
| | |
|---|---|
| H01J 37/26 | (2006.01) |
| H01J 37/28 | (2006.01) |
| H01J 37/24 | (2006.01) |
| G01N 23/225 | (2006.01) |

(52) U.S. Cl.
CPC ................. H01J 37/26 (2013.01); H01J 37/24 (2013.01); G01N 23/225 (2013.01)
USPC ........... 250/310; 250/307; 250/309; 250/311; 250/396 R; 250/397; 250/396 ML; 250/306

(58) Field of Classification Search
CPC ... H01J 37/073; H01J 37/147; H01J 37/1471; H01J 37/185; H01J 37/20; H01J 37/26; H01J 37/263; H01J 37/265; H01J 37/268; H01J 37/29; H01J 37/3045; H01J 37/3174; G01N 23/225; G01N 2021/213; G01N 21/211; G01N 2223/07; G01N 2223/414; G01N 2223/6116; G01N 23/203; G01N 23/2251
USPC ............ 250/310, 307, 397, 311, 306, 396 R, 250/492.3, 398, 492.1, 208.1, 210, 252.1, 250/372, 385.1, 396 ML, 399, 442.11, 492.2
See application file for complete search history.

(56) References Cited

U.S. PATENT DOCUMENTS

| | | | | |
|---|---|---|---|---|
| 3,597,607 A | * | 8/1971 | Campbell et al. ............. | 250/307 |
| 4,588,890 A | * | 5/1986 | Finnes ......................... | 250/307 |

(Continued)

FOREIGN PATENT DOCUMENTS

| | | |
|---|---|---|
| JP | 05-299048 | 11/1993 |
| JP | 2001-298036 | 10/2001 |

(Continued)

OTHER PUBLICATIONS

Office action issued by Japanese Patent Office for counterpart Japanese application and its English translation.

*Primary Examiner* — David A Vanore
(74) *Attorney, Agent, or Firm* — Muramatsu & Associates

(57) ABSTRACT

An electron beam is irradiated on an observation region of a sample surface. An image (SEM image) is acquired based on a detection signal of secondary electrons from a detector disposed obliquely above the observation region. A length of a shadow of a pattern appearing in the image is detected. Then, a height H of the pattern is calculated by a formula $H=L\times\tan\theta$ on the basis of the detected length L of the shadow and an apparent angle $\theta$ of the detector to the sample surface obtained in advance. An intensity distribution of the secondary electrons on a line orthogonal to an edge of the pattern is extracted, and the length L of the shadow of the pattern is obtained as a distance between two points where a recess portion of the intensity distribution intersects a predetermined threshold.

12 Claims, 15 Drawing Sheets

(56) References Cited

U.S. PATENT DOCUMENTS

| | | | |
|---|---|---|---|
| 4,670,652 A * | 6/1987 | Ichihashi et al. | 250/310 |
| 4,767,926 A | 8/1988 | Murakoshi et al. | |
| 4,803,357 A * | 2/1989 | Brust | 250/310 |
| 4,912,313 A * | 3/1990 | Kato et al. | 250/307 |
| 5,001,344 A * | 3/1991 | Kato et al. | 250/307 |
| 5,046,110 A * | 9/1991 | Carucci et al. | 382/149 |
| 5,182,454 A * | 1/1993 | Matsuda et al. | 250/310 |
| 5,627,367 A * | 5/1997 | Sofield | 250/252.1 |
| 5,892,224 A * | 4/1999 | Nakasuji | 250/310 |
| 7,095,022 B2 * | 8/2006 | Nakasuji et al. | 250/310 |
| 7,205,559 B2 * | 4/2007 | Hamashima et al. | 250/492.3 |
| 7,276,692 B2 * | 10/2007 | Katsumura et al. | 250/310 |
| 7,368,713 B2 * | 5/2008 | Matsui | 250/310 |
| 7,399,964 B2 * | 7/2008 | Shishido et al. | 250/310 |
| 7,449,690 B2 * | 11/2008 | Nishiyama et al. | 250/310 |
| 7,454,221 B1 * | 11/2008 | McKinnell et al. | 455/514 |
| 7,638,767 B2 * | 12/2009 | Yamaguchi et al. | 250/311 |
| 8,080,790 B2 * | 12/2011 | Yamazaki et al. | 250/311 |
| 8,153,969 B2 * | 4/2012 | Fukada et al. | 250/311 |
| 8,207,498 B2 * | 6/2012 | Fukuda et al. | 250/306 |
| 8,212,224 B2 * | 7/2012 | Fujisawa et al. | 250/397 |
| 8,350,213 B2 * | 1/2013 | Wang et al. | 250/310 |
| 2005/0253080 A1 * | 11/2005 | Janik | 250/372 |
| 2005/0263703 A1 * | 12/2005 | Hiroi et al. | 250/310 |
| 2007/0164226 A1 * | 7/2007 | Hamashima et al. | 250/385.1 |
| 2011/0101223 A1 * | 5/2011 | Fukuda et al. | 250/310 |
| 2012/0112066 A1 * | 5/2012 | Ogiso et al. | 250/307 |
| 2012/0217392 A1 * | 8/2012 | Murakawa et al. | 250/307 |
| 2012/0318976 A1 * | 12/2012 | Matsumoto et al. | 250/307 |

FOREIGN PATENT DOCUMENTS

| | | |
|---|---|---|
| JP | 2003-157790 | 5/2003 |
| JP | 2006-064421 | 3/2006 |
| JP | 2009-135273 | 6/2009 |

* cited by examiner $H = L \times \tan\theta$

PATTERN-HEIGHT MEASURING APPARATUS AND PATTERN-HEIGHT MEASURING METHOD

CROSS-REFERENCE TO RELATED APPLICATIONS

This application is based on and claims priority of Japanese Patent Application No. 2011-041674 filed on Feb. 28, 2011, the entire contents of which are incorporated herein by reference.

FIELD OF THE INVENTION

The embodiments discussed herein are related to a pattern-height measurement apparatus and a pattern-height measuring method, and particularly to a pattern-height measurement apparatus and a pattern-height measuring method for measuring the height of a pattern by irradiating a surface of a sample with an electron beam.

BACKGROUND ART

In recent years, mask patterns have become finer and thinner along with the progress in size reduction of semiconductor devices. Thus, not only the two-dimensional measurement of a mask pattern shape such as a line width, but also the measurement of the height of the mask pattern which affects transfer characteristics and the like is becoming increasingly important.

Techniques for measuring the height of the pattern include: (1) a method of detecting the height by observing a cross section of a sample with a scanning electron microscope (SEM); (2) a method of measuring the height with an atomic force microscope (AFM); (3) a method of measuring the height by capturing a plurality of SEM images with different focus conditions and subjecting the SEM images to image processing as disclosed by Japanese Laid-open Patent Publication No. 05-299048; and the like.

However, the method (1) in which the cross section of the sample is observed with the SEM has the following problems. A long time is required to start the observation of the cross section, and the sample used in the measurement cannot be used as a product since this method is a destructive inspection.

Moreover, in the method (2) of measuring the height with the AFM, although the sample can be measured in a nondestructive manner, a long time is required for the measurement and the throughput is low. In addition, the method (2) has a problem that a probe wears down as the number of times of the measurement increases and the measurement accuracy thereby deteriorates.

Furthermore, the method (3) using the SEM images captured with different focus conditions has a problem that accurate measurement cannot be performed when the thickness of the pattern is smaller than the focal depth of the SEM.

SUMMARY OF THE INVENTION

In view of the above problems, an object of the present invention is to provide a pattern-height measurement apparatus and a pattern-height measuring method with which the height of a pattern can be measured quickly in a nondestructive manner.

An aspect of the invention is a pattern-height measurement apparatus which includes: an electron beam scanning unit configured to irradiate a surface of a sample with an electron beam while scanning the electron beam over the surface of the sample; a detector disposed above the surface of the sample and configured to detect an intensity of secondary electrons emitted from the surface of the sample by the irradiation of the electron beam; a signal processing unit configured to generate image data on the basis of a detection signal of the detector, where the image data is obtained by capturing an image of the surface of the sample; an image processing unit configured to extract intensity distribution of the secondary electrons along a line intersecting with an edge of a pattern formed on the surface of the sample on the basis of the image data, and to detect a length of a shadow of the pattern on the basis of the intensity distribution of the secondary electrons near the edge; and a calculating unit configured to calculate a height of the pattern on the basis of the length of the shadow detected by the image processing unit.

In the pattern-height measurement apparatus according to the aspect, a plurality of the detectors may be arranged around an optical axis of the electron beam, and the signal processing unit may generate a plurality of pieces of the image data on the surface of the sample on the basis of detection signals from the plurality of detectors which are taken respectively in directions different from each other. In this case, the image processing unit may extract the intensity distribution of the secondary electrons from the image data taken in a direction orthogonal to the edge of the pattern.

Meanwhile, the image processing unit may detect any one of the following as the length of the shadow, namely, (1) a distance between two points where the intensity distribution of the secondary electrons near the edge intersects a predetermined threshold, (2) a distance between a minimum value portion of the intensity distribution of the secondary electrons and a point on a side away from the pattern where the intensity distribution of the secondary electrons near the edge intersects a predetermined threshold, (3) a square root of an area of a region surrounded by the intensity distribution of the secondary electrons near the edge and a straight line indicating a predetermined threshold, and (4) a distance between either an upper end or an lower end of the edge of the pattern and a point on a side away from the pattern where the intensity distribution of the secondary electrons near the edge intersects a predetermined threshold. In any of these cases, the threshold can be set within a range higher than a minimum value in a recess portion of the intensity distribution of the secondary electrons near the edge and lower than an intensity of the secondary electrons in a flat portion adjacent to the recess potion of the intensity distribution of the secondary electrons.

Moreover, the calculating unit may calculate the height of the pattern on the basis of the length of the shadow and an apparent angle of the detector to the surface of the sample. Meanwhile, the calculating unit may calculate the height of the pattern by adding a predetermined offset value determined by the material of the surface of the sample to the length of the shadow.

Another aspect of the invention is a pattern-height measurement method including the steps of: irradiating a surface of a sample with an electron beam while scanning the electron beam over the surface of the sample, and detecting an intensity of secondary electrons emitted from the surface of the sample by the irradiation of the electron beam using a detector disposed above the surface of the sample; generating image data on the basis of a detection signal of the detector, where the image data is obtained by capturing an image of the surface of the sample; extracting intensity distribution of the secondary electrons along a line intersecting with an edge of a pattern formed on the surface of the sample on the basis of the image data, and detecting a length of a shadow of the pattern on the basis of a recess portion of the intensity distribution of the secondary electrons; and calculating a height of the pattern on the basis of the length of the shadow.

In the pattern-height measurement apparatus and the pattern-height measuring method of the above-described aspects, the length of the shadow appearing in the edge portion of the pattern is detected from the image data obtained by scanning the electron beam over the surface of the sample, and the height of the pattern is detected based on the length of the shadow. Thus, the height of the pattern can be measured quickly in a nondestructive manner.

DESCRIPTION OF EMBODIMENTS

Embodiments of the present invention are described below with reference to the drawings.

First Embodiment

Figure 1:
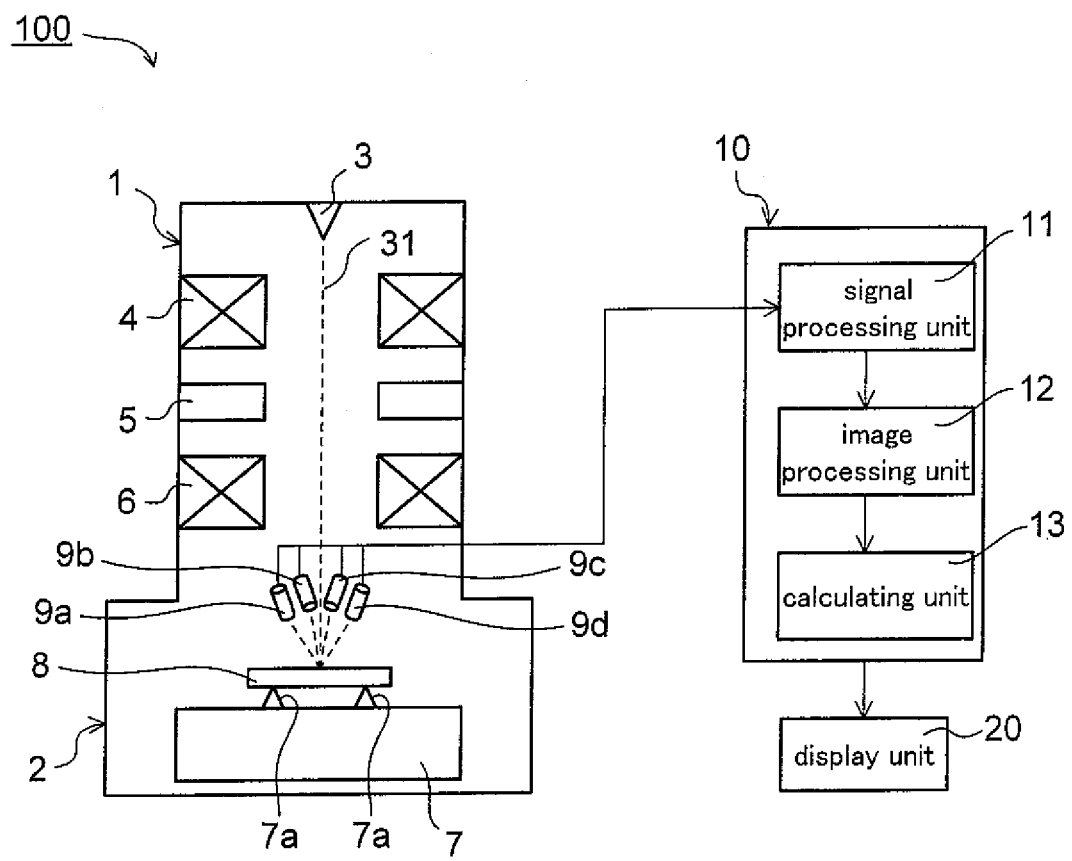
FIG. 1 is a block diagram showing a pattern-height measurement apparatus of a first embodiment.
Figure 2:
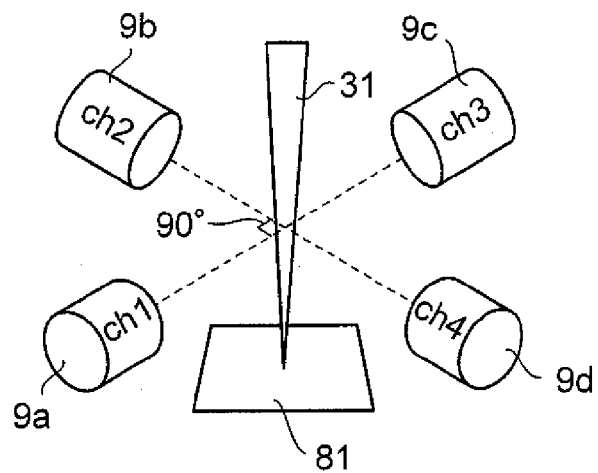
FIG. 2 is a schematic view showing an arrangement of detectors of the pattern-height measurement apparatus of FIG. 1.

FIG. 1 is a block diagram showing a pattern-height measurement apparatus of a first embodiment and FIG. 2 is a schematic view showing an arrangement of detectors of the pattern-height measurement apparatus.

As shown in FIG. 1, a pattern-height measurement apparatus 100 of the embodiment includes: a chamber 2 configured to house a sample 8 therein; an electron beam scanning unit 1 configured to irradiate the sample 8 with an electron beam 31; and a control unit 10 configured to control parts of the pattern-height measurement apparatus 100 and to perform processing of measurement data.

The chamber 2 is provided with a stage 7 configured to hold the sample 8 such as a wafer or a photomask via a supporting body 7a. The stage 7 can move the sample 8 on the basis of a control signal from the control unit 10 in such a way that an observation region of the sample 8 is moved to be within an electron beam irradiation area of the electron beam scanning unit 1.

The electron beam scanning unit 1 has an electron gun 3. The electron beam 31 is emitted from the electron gun 3 at a predetermined accelerating voltage. The electron beam 31 is converged by a condensing lens 4, positioned by a deflection coil 5, and then focused by an objective lens 6 in such a way that a surface of the sample 8 is irradiated with the electron beam 31.

In addition, the electron beam scanning unit 1 is provided with first to fourth electron detectors 9a to 9d for detecting secondary electrons emitted by irradiating the surface of the sample 8 with the electron beam 31.

As shown in FIG. 2, the first to fourth electron detectors 9a to 9d are disposed symmetrically around the optical axis of the electron beam 31 with 90° intervals. Here, it is assumed that the detectors 9a to 9d are arranged in directions along the diagonal lines of a rectangular observation region 81. The detectors 9a to 9d are formed of scintillators, for example, and output intensities of the detected secondary electrons as signals ch1 to ch4, respectively.

Meanwhile, as shown in FIG. 1, the control unit 10 is provided with a signal processing unit 11, an image processing unit 12, and a calculating unit 13.

The signal processing unit 11 coverts the signals ch1 to ch4 transmitted from the detectors 9a to 9d into digital signals, and generates pieces of image data (SEM images) on the basis of these digital signals.

Figure 3:
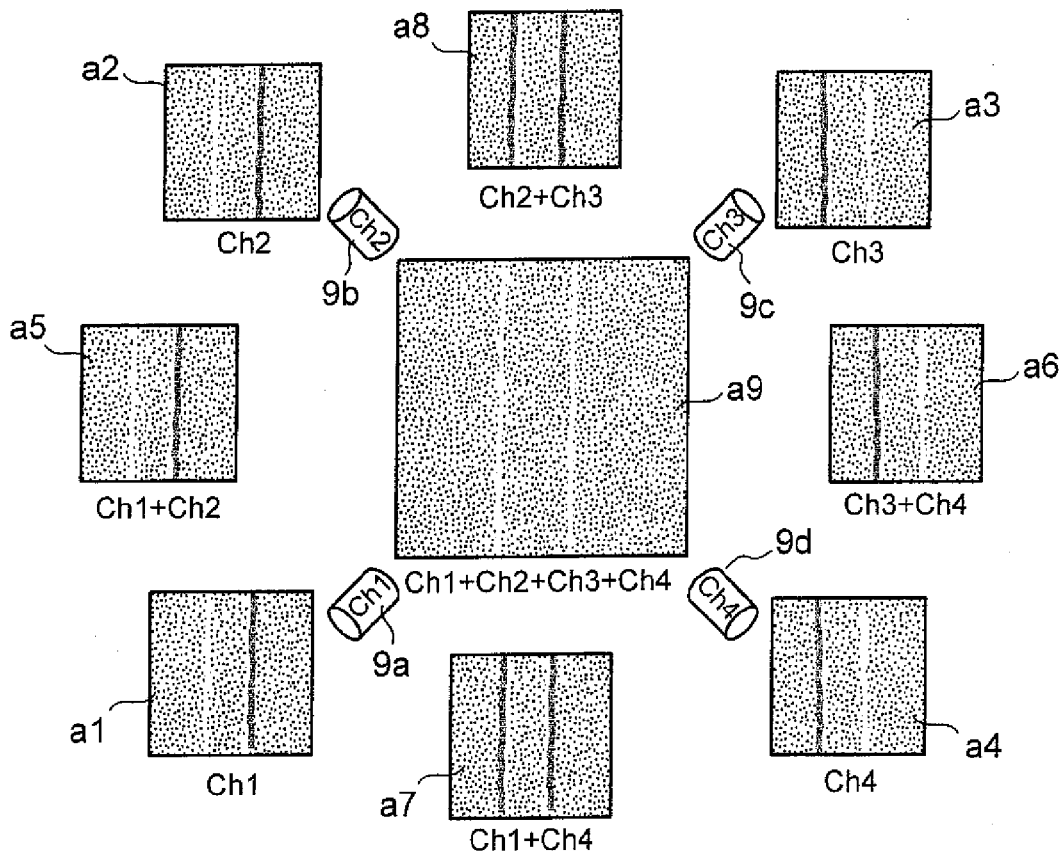
FIG. 3 is a schematic view showing an example of pieces of image data generated by a signal processing unit of the pattern-height measurement apparatus of FIG. 1.

FIG. 3 is a schematic view showing an example of the pieces of image data generated by the signal processing unit 11.

As shown in FIG. 3, the signal processing unit 11 generates a lower left image a1, an upper left image a2, an upper right image a3, and a lower right image a4 on the basis of the signals ch1 to ch4, the images respectively corresponding to SEM images of the observation region 81 taken from lower left, upper left, upper right, and lower right.

Moreover, the signal processing unit 11 adds the signals from every two of the adjacent detectors to each other, and generates a left image a5, a right image a6, a lower image a7, and an upper image a8 respectively corresponding to SEM images taken in directions in the middle of every two of the adjacent detectors 9a to 9d (left, right, low, and up). Specifically, the left image a5 is generated by adding the signals ch1 and ch2 to each other, the right image a6 is generated by adding the signals ch3 and ch4 to each other, the lower image a7 is generated by adding the signals ch1 and ch4 to each other, and the upper image a8 is generated by adding the signals ch2 and ch3 to each other.

Furthermore, the signal processing unit 11 generates a full-added image a9 by summing all of the signals ch1 to ch4. The full-added image a9 is an image similar to a secondary electron image obtained by a conventional scanning electron microscope, and no shadow is displayed in edges of a pattern.

Generated images a1 to a9, as described above, are displayed on a display unit 20 (see FIG. 1).

The image processing unit 12 (see FIG. 1) of the control unit 10 extracts an intensity profile (line profile) of the secondary electrons along a line intersecting an edge of the pattern, on the basis of the image data generated by the signal processing unit 11. Then, the image processing unit 12 detects the length of a shadow of the pattern on the basis of the extracted line profile.

Moreover, the calculating unit 13 calculates the height of the pattern on the basis of the length of shadow of the pattern which is detected by the image processing unit 12.

The principle of height measurement of the pattern of the embodiment is described below.

Figure 4A:
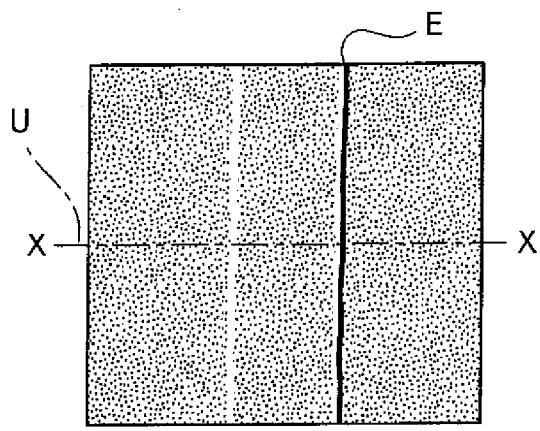
FIGS. 4A to 4C are schematic views showing the principle of height measurement of a pattern of the first embodiment.
Figure 4B:
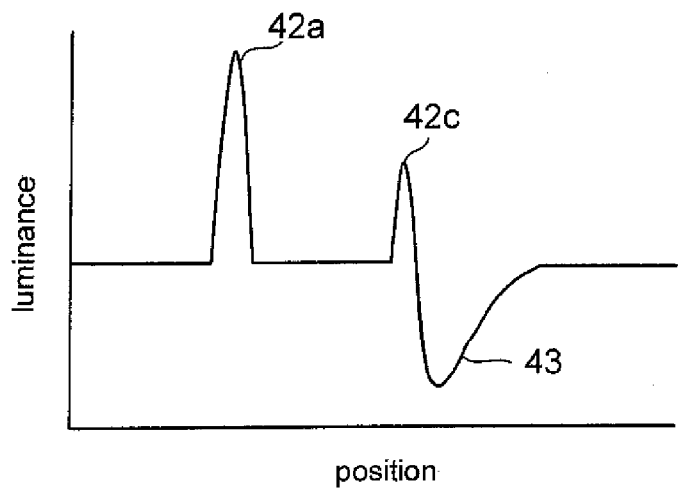

FIG. 4A is a view showing the left image a5 of a line pattern extending in an up-down direction, and FIG. 4B is a graph showing an intensity distribution (line profile) of secondary electrons on the line X-X of FIG. 4A. Moreover, FIG. 4C is a schematic view for explaining a relation between the length of the shadow of the pattern and the height of the pattern.

In a secondary electron image of a conventional scanning electron microscope, many secondary electrons emerge in a sidewall portion of the pattern, and edges extending in all directions are displayed white at a high luminance. However, as shown in FIGS. 4A and 4B, in the left image a5 taken by the pattern-height measurement apparatus 100 of the embodiment, a left edge portion of the line pattern is displayed at a high luminance (protruding portion 42a) while a black shadow at a low luminance appears in a right edge portion E (recess portion 43) of the line pattern.

The reason for this is conceived as follows. As shown in FIG. 4C, a right sidewall 82b of a line pattern 82 serves as a barrier and thus secondary electrons emitted near the right sidewall 82b are prevented from reaching a virtual detector 99a which correspond to the left image a5.

Figure 4C:
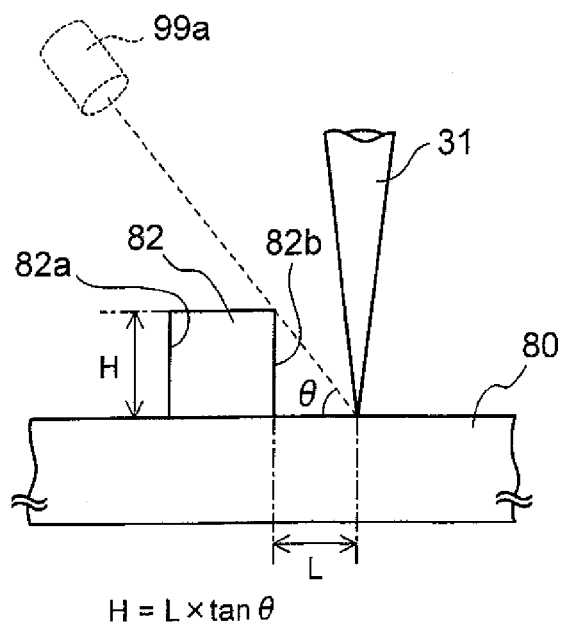

In FIG. 4C, an angle θ indicates an apparent angle of the virtual detector 99a with respect to a sample surface. It is conceived that the apparent angle θ of the virtual detector 99a is constant for the same type of samples, and that a region (length of shadow) L, in which the line pattern 82 prevents the detection of the secondary electrons, changes depending on the height H of the line pattern 82. Thus, in the embodiment, the height H of the pattern 82 is obtained by using the formula H=L× tan θ, on the basis of the length L of the shadow of the pattern 82 and the apparent angle θ of the virtual detector 99a.

The length L of the shadow can be obtained as follows. The intensity distribution (line profile, FIG. 4B) of the secondary electrons along a line U (line X-X) intersecting the pattern of FIG. 4A is acquired, and then the length L is obtained from a curve (recess portion 43) of the acquired line profile near the edge.

Moreover, the apparent angle θ of the virtual detector 99a is obtained from the formula θ=tan$^{-1}$H$_A$/L on the basis of a pattern height H$_A$ and the length L of the shadow. Here, the pattern height H$_A$ is obtained by preparing a reference sample made of the same material as a measurement target and then measuring a pattern on the reference sample in advance with an AFM, a film thickness meter or the like, the length L of the shadow is obtained from the image data generated by the pattern-height measurement apparatus 100. The apparent angle θ of the virtual detector 99a varies depending on the materials of the pattern 82 and a substrate 80. Thus, it is preferable to obtain the apparent angle θ of the virtual detector 99a through an experiment every time the materials are changed.

In the pattern-height measurement apparatus 100 of the embodiment, the images of the observation region taken from a plurality of directions can be acquired. Thus, the pattern-height measurement apparatus 100 can detect not only the height of the pattern extending in the up-down direction but also the heights of patterns with various shapes. In this arrangement, the height of a pattern can be measured on the basis of the principle described above by using an image taken in a direction orthogonal to an edge of the pattern.

Figure 5:
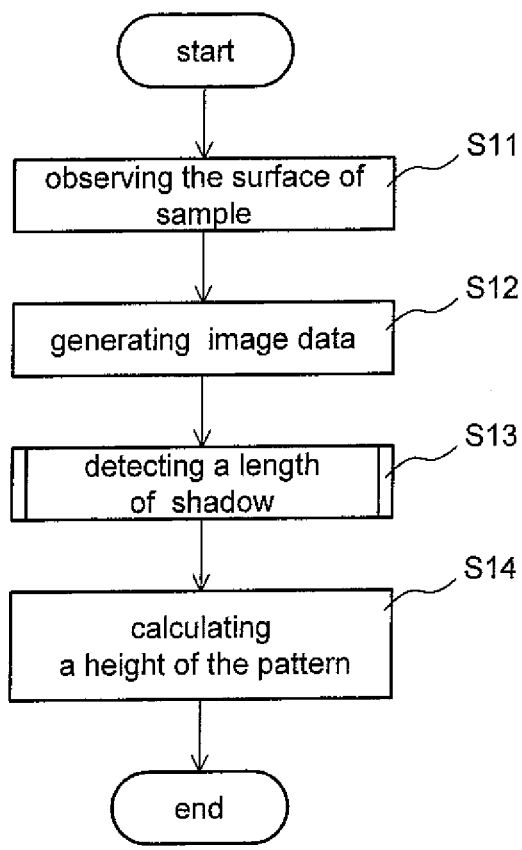
FIG. 5 is a flowchart showing a method of measuring the height of the pattern with the pattern-height measurement apparatus of the first embodiment.

Descriptions are given below of a method for measuring the height of the pattern with the pattern-height measurement apparatus 100 of the embodiment. FIG. 5 is a flowchart showing the method for measuring the height of the pattern with the pattern-height measurement apparatus 100 of the embodiment.

First, in step S11 of FIG. 5, the electron beam scanning unit 1 irradiates the observation region 81 of the sample 8 with the electron beam 31 and scans the electron beam 31 over the observation region 81. The secondary electrons emitted from the surface of the observation region 81 by the irradiation of the electron beam 31 are captured by the detectors 9a to 9d. The intensities of the secondary electrons at respective irradiation positions are sent as the signals ch1 to ch4 to the signal processing unit 11 of the control unit 10.

Next, in step S12, the signal processing unit 11 converts the signals ch1 to ch4 outputted from the detectors 9a to 9d into digital signals, and the images a1 to a9 (see FIG. 3) are generated based on the digital signals.

Next, in step S13, the image processing unit 12 of the control unit 10 detects the length of the shadow on the basis of the images generated by the signal processing unit 11.

Figure 6:
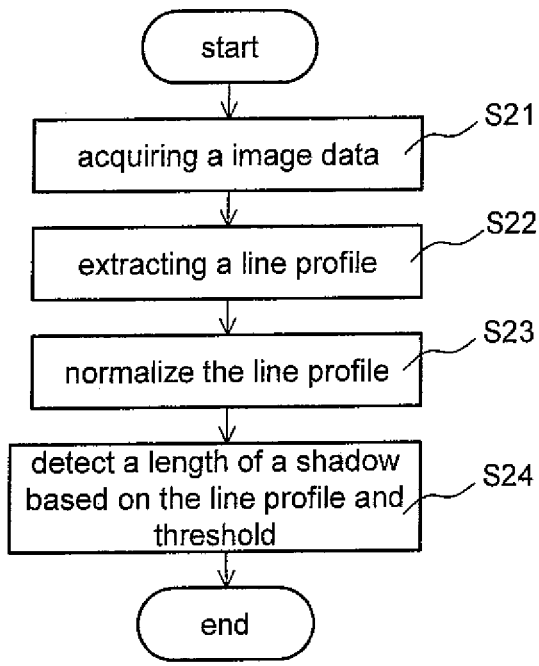
FIG. 6 is a flowchart showing a method of detecting the length of a shadow of the pattern by an image processing unit of FIG. 1.

FIG. 6 is a flowchart showing a method of detecting the length of the shadow of the pattern by the image processing unit 12.

First, in step S21, the image processing unit 12 acquires the image data taken in the direction orthogonal to the edge of the pattern to be measured.

For example, as shown in FIG. 4A, the left image a5 is obtained in the case of the line pattern extending in the up-down direction. Note that the right image a6 may be obtained instead of the left image a5.

Next, in step S22, the image processing unit 12 extracts the intensity distribution (line profile) of the secondary electrons along a line orthogonal to the edge of the pattern from the image data acquired in step S21. For example, in the case of the line pattern of FIG. 4A, the line profile on the line X-X is extracted. Note that when only one line profile is used, the measurement may be affected by local roughness of the edge of the pattern. Accordingly, in the case where higher accuracy is required, the line profile may be obtained by averaging the intensity distributions of the secondary electrons along a plurality of lines.

Figure 7:
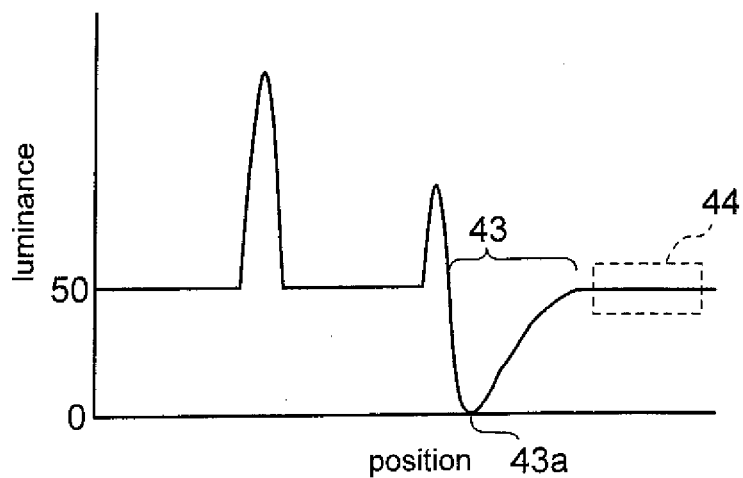
FIG. 7 is a graph explaining a method of normalizing a line profile.

Next, in step S23 of FIG. 6, the image processing unit 12 normalizes the line profile extracted in step S22. FIG. 7 is a schematic view explaining a method of normalizing the line profile.

In this method, the image processing unit 12 detects a luminance of a minimum value 43a in the recess portion 43 of the line profile and an average luminance of a flat portion 44 adjacent to the recess portion 43. Then, as shown in FIG. 7, the image processing unit 12 shifts the luminances of the entire line profile so that the minimum value 43a becomes zero. Then, the image processing unit 12 adjusts a ratio of luminance of the line profile so that the average luminance of the flat portion 44 becomes 50. Thus, the normalization of the line profile is completed.

Next, in step S24 of FIG. 6, the image processing unit 12 sets a threshold I to a predetermined luminance, and detects the length of the shadow on the basis of the threshold I and the normalized line profile by using any one of first to third methods described below.

Figure 8A:
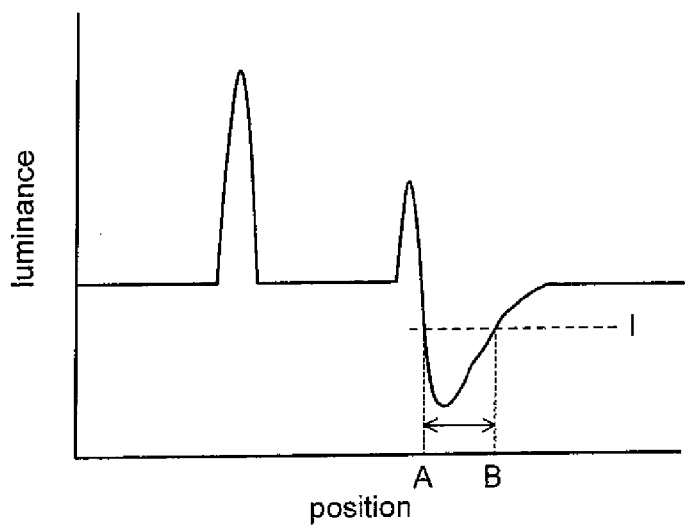
FIGS. 8A to 8C are graphs each showing a method of detecting the length of the shadow on the basis of a threshold and the line profile.
Figure 8B:
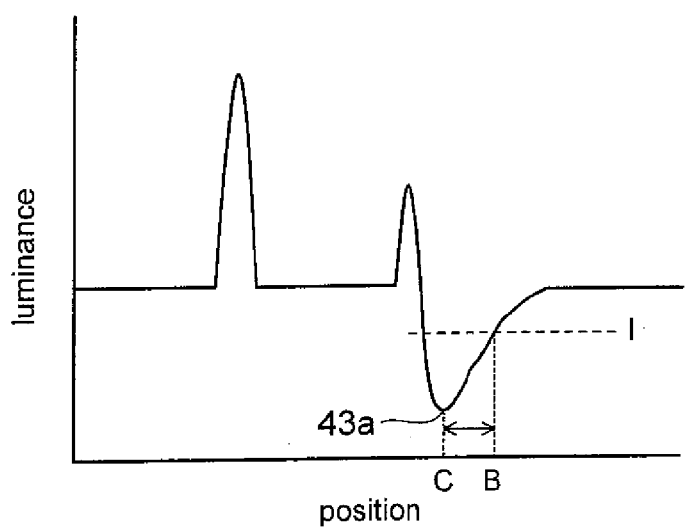
Figure 8C:
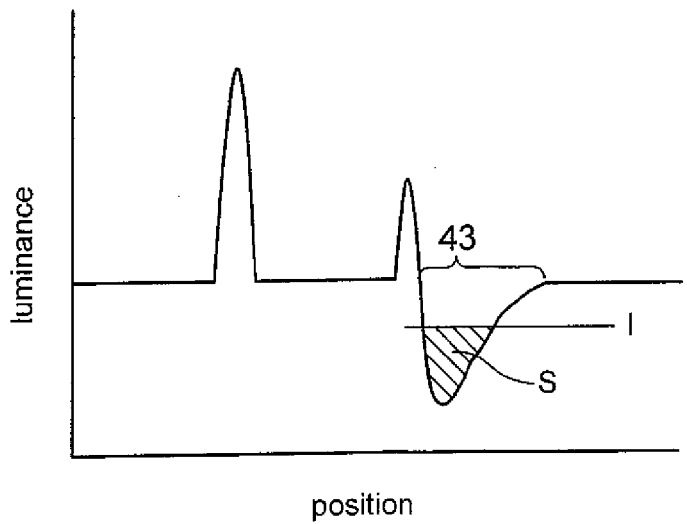

FIGS. 8A to 8C are graphs each showing a method of detecting the length of the shadow on the basis of the threshold and the line profile.

In the first method (method in which the width of the recess portion is used as a reference), as shown in FIG. 8A, positions of two points A and B where the recess portion of the line profile intersects the threshold I are obtained, and the distance between the two points A and B is detected as the length of the shadow.

In the second method (method in which the minimum value is used as a reference), as shown in FIG. 8B, the distance between the point B and a position C of the minimum value portion 43c of the line profile is detected as the length of the shadow. Here, the point B is the point located farther from the pattern out of the two points where the recess portion of the line profile intersects the threshold I. In the line profile, when the height of the pattern changes, a portion of the profile on a side of the minimum value 43a located farther from the pattern changes most drastically. Thus, the measurement sensitivity can be improved by using the second method.

In the third method (method in which an area is used as a reference), as shown in FIG. 8C, the area S of a region surrounded by recess portion 43C of the line profile and a straight line indicating the threshold I is obtained, and the square root of the area S is detected as the length of the shadow. In the third method, the length of the shadow is detected based on the area S. Thus, even when there is a small variation in the line profile at the interaction points with the threshold I, the measurement is less likely to be affected by the variation. Accordingly, the stability of measurement is improved as compared to other methods.

The detection of the length of the shadow (step S13 of FIG. 5) by the image processing unit 12 is thus completed.

Thereafter, in step S14 of FIG. 5, the calculating unit 13 obtains the height H of the pattern from the formula H=L×tan θ, on the basis of the length L of the shadow and the apparent angle θ of the detector obtained in advance, and the process of measuring the height of the pattern by the pattern-height measurement apparatus 100 is completed.

As described above, the pattern-height measurement apparatus 100 of the embodiment obtains the height of the pattern on the basis of the length of the shadow of the pattern appearing in the SEM images. Thus, the height of the pattern can be quickly measured in a nondestructive manner.

EXAMPLE 1

In Example 1, effects of the threshold I used in the detection of the length of the shadow on the measurement accuracy were examined.

Figure 9A:
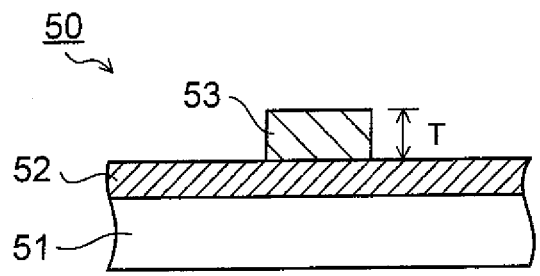
FIG. 9A is a cross-sectional view showing a structure of a first mask and FIG. 9B is a cross-sectional view showing a structure of a second mask.
Figure 9B:
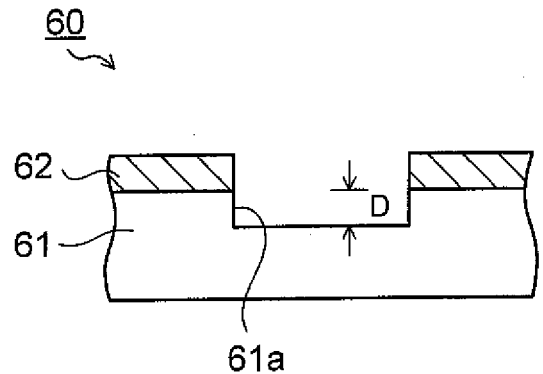

FIGS. 9A and 9B are cross-sectional views of samples used in the evaluation of Example 1. FIGS. 9A and 9B respectively show a structure of a first mask and a structure of a second mask.

As shown in FIG. 9A, a first mask 50 was formed as follows. A Cr film 52 having a thickness of about 100 nm was formed on a quartz substrate 51, and a line pattern 53 made of TaSi and having a thickness T of about 50 to 70 nm and a width of about 500 nm was formed on the Cr film 52. Here, the samples having the thickness T of the line pattern 53 respectively set to 50 nm, 60 nm, and 70 nm were prepared.

As shown in FIG. 9B, a second mask 60 was formed as follows. A TaSi film having a thickness of 70 nm was formed on a quartz substrate 61, and the TaSi film was patterned into a line pattern 62 having a width of about 400 nm. Note that part of the quartz substrate 61 was etched to form a groove 61a in the course of etching the TaSi film. Here, etching conditions were adjusted to prepare samples having various depths D of the groove 61a of the second mask 60 within the depth range of 1 to 10 nm.

Next, for each of the first mask 50 and the second mask 60, the height of the pattern was measured with the AFM and the length of the shadow of the pattern was detected by performing an observation with the pattern-height measurement apparatus 100 (see FIG. 1).

Figure 10:
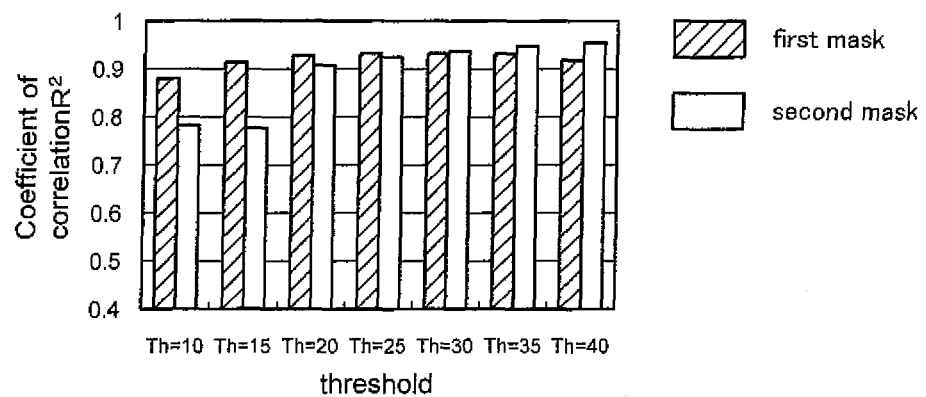
FIG. 10 is a graph showing a correlation between the height of the pattern obtained by the AFM and the length of the shadow detected by using the method (first method) shown in FIG. 8A in Example 1.

FIG. 10 is a graph showing a correlation between the length of the shadow detected by using the first method (see FIG. 8A) and the measurement result obtained by the AFM, in which the horizontal axis indicates the threshold and the vertical axis indicates a coefficient of correlation. Note that in FIG. 10, Th represents a value (luminance value) of the threshold in the normalized line profile. For example, Th=10 is equivalent to a luminance of 20% (=10/50) of the average luminance 50 of the flat portion adjacent to the recess portion on the line profile.

As shown in FIG. 10, the length of the shadow detected by using the first method has a relatively high correlation with the measurement result of the pattern height obtained by the AFM regardless of the value of the threshold. It is found from this result that a measurement which has a relatively low dependence on the threshold and which has high reproducibility can be achieved by using the first method.

Figure 11:
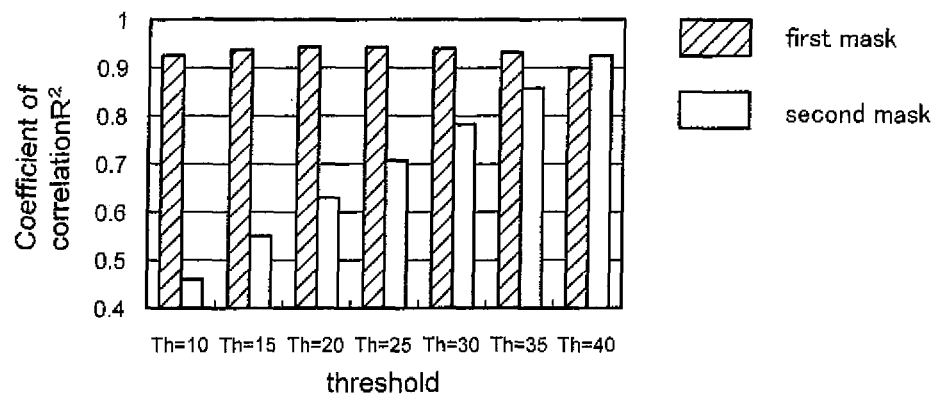
FIG. 11 is a graph showing a correlation between the height of the pattern obtained by the AFM and the length of the shadow detected by using the method (second method) shown in FIG. 8B in Example 1.

FIG. 11 is a graph showing a correlation between the length of the shadow detected by using the second method (see FIG. 8B) and the measurement result obtained by the AFM, in which the horizontal axis indicates the threshold and the vertical axis indicates the coefficient of correlation.

As shown in FIG. 11, in the case of the first mask 50, the length of the shadow detected by using the second method has a relatively high correlation with the measurement result obtained by the AFM regardless of the threshold. However, in the case of the second mask 60, the correlation between the detected length and the measurement result obtained by the AFM becomes lower as the threshold becomes smaller. It is not preferable that the measurement accuracy change depending on the threshold as described above. Thus, it is found that the detection of the length of the shadow by using the second method is not suitable for the evaluation of the pattern height of the second mask 60.

Figure 12:
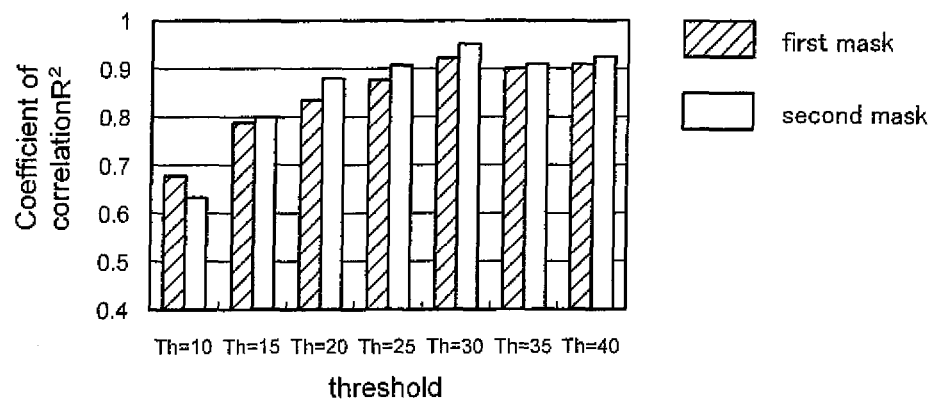
FIG. 12 is a graph showing a correlation between the height of the pattern obtained by the AFM and the length of the shadow detected by using the method (third method) shown in FIG. 8C in Example 1.

FIG. 12 is a graph showing a correlation between the length of the shadow detected by using the third method (see FIG. 8C) and the measurement result obtained by the AFM, in which the horizontal axis indicates the threshold and the vertical axis indicates the coefficient of correlation.

As shown in FIG. 12, a correlation between the length of the shadow detected by using the third method and the measurement result obtained by the AFM was low in a portion where the threshold is small. Moreover, it is found that the fluctuation in the coefficient of correlation depending on the threshold is larger than that in the case of using the first method. Thus, the measurement accuracy becomes lower than the first method when the length of the shadow obtained by using the third method is applied. An effect of the normalization of the line profile performed prior to the detection of the shadow length is a conceivable reason why the correlation between the shadow length obtained by using the third method and the pattern height becomes lower as described above. In other words, it is conceivable that the correlation between the shadow length obtained by using the third method and the pattern height becomes lower because information on the line profile in the vertical direction changes due to the normalization.

EXAMPLE 2

In Example 2, a correlation between the pattern height obtained by the AFM and the pattern height obtained from the length of the shadow was examined for each of the first mask 50 and the second mask 60 shown in FIGS. 9A and 9B. Note that in Example 2, the length of the shadow is obtained by using the first method and the threshold used in the first method is set to 25 (50% of the luminance at the flat portion).

In Example 2, the apparent angle θ of the detector is obtained by using four samples having different thicknesses of the pattern for each of the first mask 50 and the second mask 60. As a result, it was found that the apparent angle θ of the detector for the first mask 50 was 66.2° and that for the second mask 60 was 63.2°.

Next, the first mask 50 and the second mask 60 each having a pattern thickness different from those described above were prepared. For each of the first mask 50 and second mask 60, the length L of the shadow was obtained by using the first method and the height of the pattern was calculated by using the apparent angle θ of the detector which had been obtained in advance. Moreover, the heights of the same patterns were measured with the AFM.

Figure 13A:
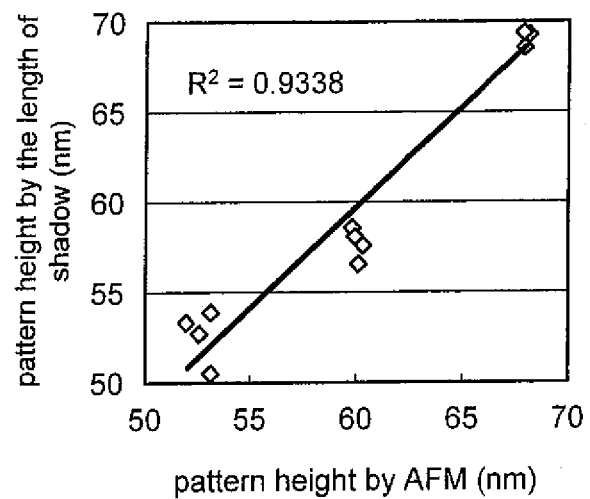
FIGS. 13A and 13B are graphs each showing a correlation between the height of the pattern obtained by the AFM and the height of the pattern obtained on the basis of the length of the shadow by using the first method in Example 2.

FIG. 13A is a graph which shows a measurement result of the first mask 50. In FIG. 13A, the horizontal axis indicates the pattern height obtained by the AFM and the vertical axis indicates the height of the pattern obtained from the SEM image. Similarly, FIG. 13B is a graph which shows a measurement result of the second mask 60.

Figure 13B:
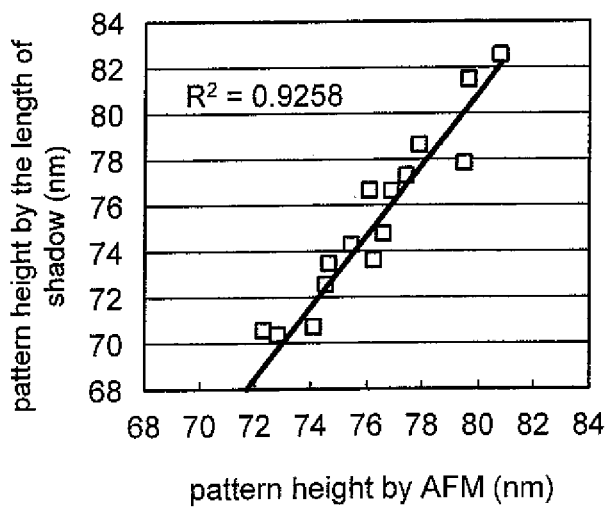

As shown in FIGS. 13A and 13B, it is confirmed that the measurement result obtained from the length of the shadow has an excellent correlation with the measurement result obtained by the AFM for each of the first mask 50 and second mask 60.

Modified Example of First Embodiment

In the aforementioned description, the calculating unit 13 obtains the height H of the pattern by multiplying the length L of the shadow by tan θ. Alternatively, the height H of the pattern can be obtained by adding a certain offset value $L_{off}$ to the length L of the shadow as in the modified example.

The offset value $L_{off}$ can be obtained experimentally by subtracting the length L of the shadow of the pattern which is obtained by the pattern-height measurement apparatus 100 from the pattern height $H_A$ obtained by the measurement with the AFM. The offset value $L_{off}$ varies depending on the material of the sample surface. Thus, it is preferable that the offset value $L_{off}$ be obtained before the measurement every time the material of the sample to be evaluated is changed.

EXAMPLE 3

In Example 3, descriptions are given of an example in which the pattern height is obtained by using the method of the modified example of the first embodiment.

In Example 3, a sample was prepared as follows. A light shielding film made of chromium oxide having a thickness of 100 nm was formed on a 6-inch-square quartz substrate being subjected to optical grinding, and a line pattern having a width of about 200 nm was formed by patterning the light shielding film.

Next, the height $H_A$ of the pattern of the sample of Example 3 was measured with the AFM, and the length L of the shadow of the pattern was detected with the pattern-height measurement apparatus 100 by using the second method (see FIG. 8B). Then, the offset value $L_{off}$ was obtained by calculating the difference between the values of the height $H_A$ and the value of the length L. Consequently, the offset value $L_{off}$ of the sample of Example 3 was equal to 31.4 nm.

Figure 14:
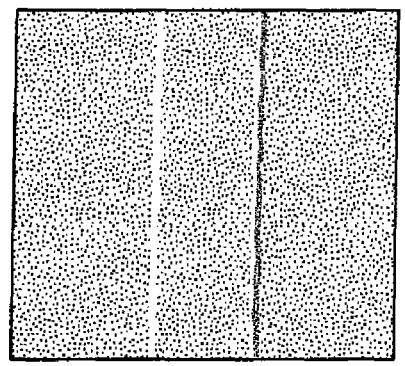
FIG. 14 is a view showing a left image of a sample of Example 3.

Next, another portion of the sample of Example was selected as the measurement region, and an observation was performed on the selected measurement region with the pattern-height measurement apparatus 100. FIG. 14 shows the left image a5 of the sample of Example 3.

Figure 15:
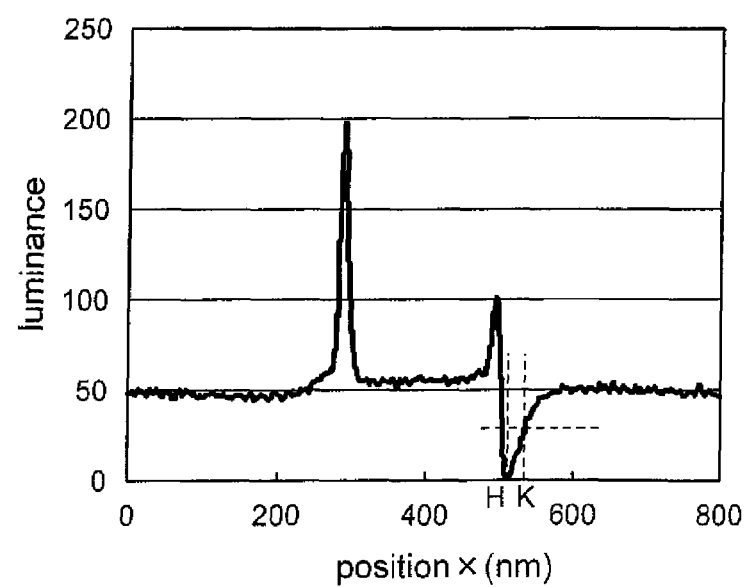
FIG. 15 is a graph showing a line profile (normalized) extracted from FIG. 14.

Subsequently, the line profile is extracted from the left image a5 of FIG. 14 and is normalized. FIG. 15 is a graph showing the normalized line profile of Example 3.

Then, the position H of the minimum value of the line profile and the position of a point K where the recess portion of the line profile intersects the threshold are obtained and the distance between the position H and the point K is obtained as the length of the shadow on the basis of the line profile of FIG. 15 by using the second method. Consequently, the length of the shadow was 67.7 nm.

The offset value of 31.4 nm was added to the length of the shadow of 67.7 nm which was obtained as described above, and thus the height of pattern of Example 3 was equal to 99.1 nm.

Meanwhile, the height of the line pattern of FIG. 15 was 99.8 nm when measured with the AFM. It is confirmed from these results that the height of the pattern can be accurately measured by using the method shown in the modified example of the first embodiment.

Second Embodiment

In a second embodiment, descriptions are given of a method of detecting a length of a shadow while considering an effect of an inclination angle of a sidewall of a pattern. Note that since portions of the embodiment other than the method of detecting the length of the shadow are the same as those of the first embodiment, descriptions of the same portions are omitted.

The inventors of the present application prepared samples with different inclination angles to examine the effect of the inclination angle of the sidewall of the pattern on measurement results, and detected the length of the shadow of each sample with the pattern-height measurement apparatus 100 of FIG. 1. Note that the length of the shadow was detected by using the first method shown in FIG. 8A.

Figure 16:
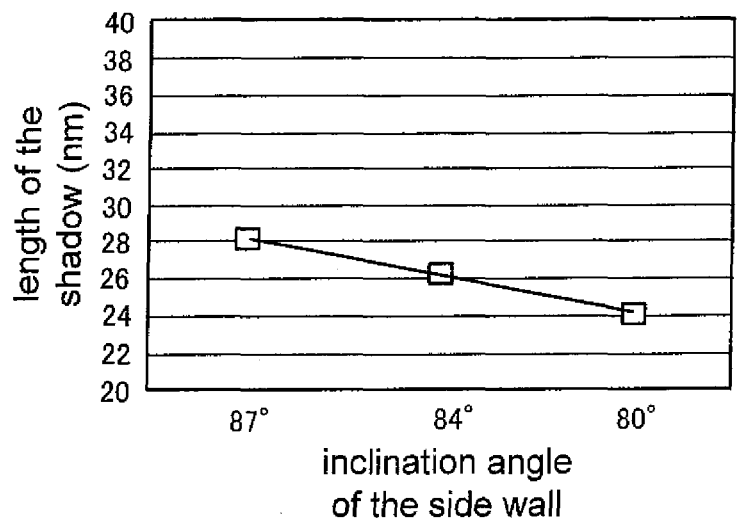
FIG. 16 is a graph showing a relation between an inclination angle of a sidewall of the pattern and the length of the shadow of the pattern which is obtained by using the first method.

FIG. 16 is a graph showing a relation between the inclination angle of the sidewall of the pattern and the length of the shadow of the pattern.

As shown in FIG. 16, the length of the shadow detected by using the first method becomes smaller as the inclination angle of the sidewall becomes smaller. Accordingly, when the length of the shadow is detected by using the first method, the length of the shadow changes depending on the inclination angle of the sidewall of the pattern. Thus, an error may occur when the first method is used for a sample having a wide variation in the inclination angle of the sidewall.

Figure 17:
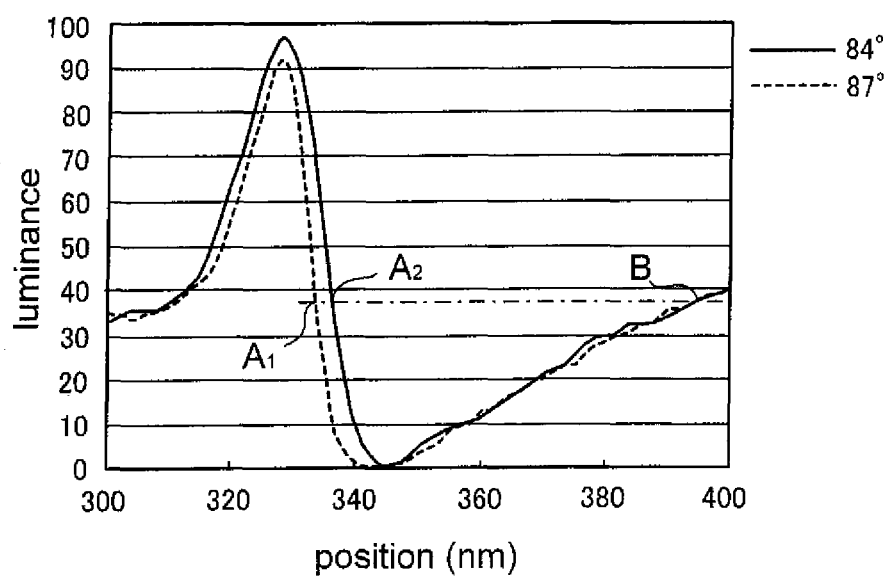
FIG. 17 is a graph showing line profiles of patterns whose sidewalls respectively have inclination angles of 87° and 84°, and shows portions near the sidewalls in an enlarged manner.

FIG. 17 is a graph showing line profiles of patterns whose sidewalls respectively have inclination angles of 87° and 84°, and shows portions near the sidewalls in an enlarged manner.

As shown in FIG. 17, even if the inclination angle of the sidewall changes, the intensity distribution of secondary electrons hardly changes in a region on a side of the minimum value portion away from the pattern (region on the right of the minimum value in the graph). On the other hand, it is found that the intensity distribution of secondary electrons changes due to a change in the inclination angle of the sidewall in a region (region on the left of the minimum value in the graph) closer to the pattern than the minimum value portion of the line profile.

A conceivable reason for this is that a region from which the secondary electrons are emitted changes near an upper end of the sidewall of the pattern depending on the inclination angle of the sidewall. Specifically, it is conceivable that the emission efficiency of the second electrons increases near the upper end of the sidewall of the pattern by a so-called edge effect. Such a region increasing the emission efficiency of the second electrons conceivably spreads farther to a portion away from near the upper end of the sidewall of the pattern as the inclination angle of the sidewall becomes smaller.

Such a change in the line profile causes positions of respective points A1 and A2, each of which is the one closer to the pattern of the two points where recess portion of the line profile intersects with the threshold I, to shift farther away from the pattern as the angle becomes smaller. Thus, the length of the shadow becomes smaller as the inclination angle of the sidewall of the pattern becomes smaller.

In order to prevent such a problem, a reference point for detecting the length of the shadow is desirably set in a portion not affected by the inclination angle of the sidewall of the pattern.

Thus, in the embodiment, the inventors focused on an upper end or a lower end of the sidewall of the pattern as the reference point for detecting the length of the shadow. A method of detecting the length of the shadow of the pattern of the embodiment is described below.

Figure 18:
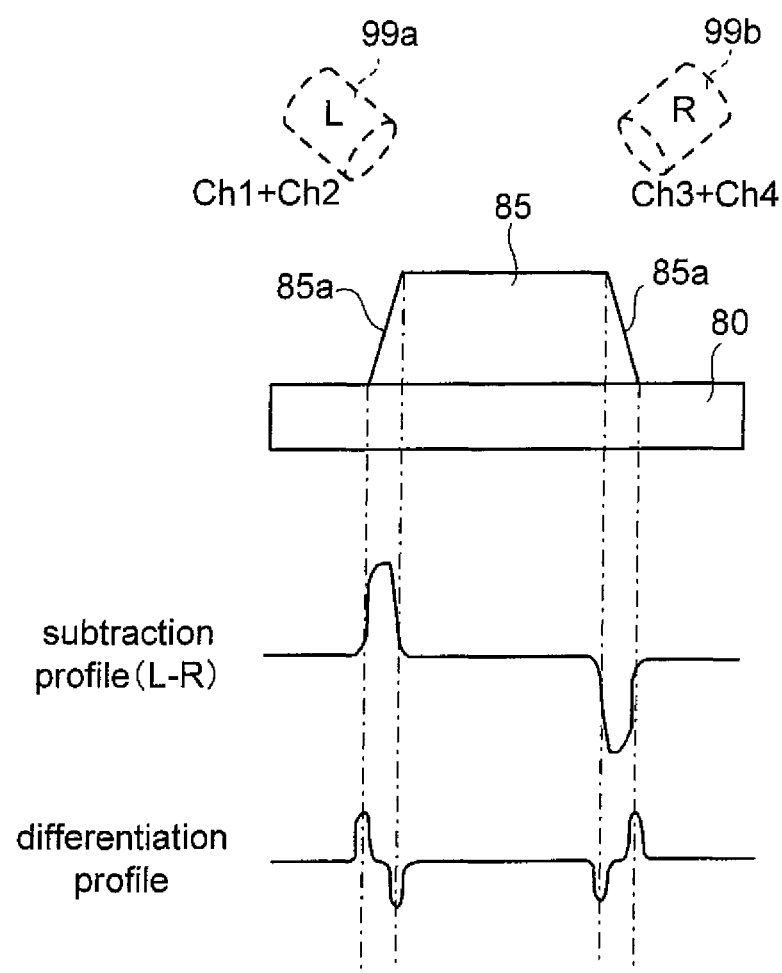
FIG. 18 is a schematic view explaining a method of detecting positions of an upper end and a lower end of a sidewall of a pattern in a second embodiment.

FIG. 18 is a schematic view explaining a method of detecting positions of the upper end and the lower end of the sidewall of the pattern in the embodiment.

In the embodiment, the image processing unit 12 detects the upper end and lower end of the sidewall of the pattern on the basis of pieces of image data of the pattern which are respectively taken from two directions. Descriptions are given of an example in which a pattern extending in the up-down direction is detected by using the left image a5 and the right image a6.

First, the image processing unit 12 acquires the left image a5 and the right image a6 taken respectively by the virtual detectors 99a and 99b disposed in directions orthogonal to sidewalls 85a of a pattern 85 as shown in FIG. 18. Then, the line profile along a predetermined line orthogonal to the edges of the pattern is extracted from each of the images a5 and a6.

Next, a subtraction between the line profile of the left image a5 and the line profile of the right image a6 is calculated, and a subtraction profile is obtained as shown in a middle section of FIG. 18. In the subtraction profile, a portion corresponding to each of the sidewalls 85a of the pattern 85 appears as a protruding portion or a recess portion.

Next, the subtraction profile described above is differentiated to obtain a differentiation profile as shown in a lower section of FIG. 18. The differentiation profile reflects a rate of change in inclination of a sample surface. The protruding portion or the recess portion appears in a portion corresponding to the upper end or lower end of each sidewall 85a where the rate of change in inclination becomes the largest. Thus, the position of the upper end of each sidewall 85a can be determined by the position of the minimum value of the differentiation profile. Moreover, the position of the lower end of each sidewall 85a can be determined by the position of the maximum value of the differentiation profile. The positions of the maximum value and the minimum value of the differentiation profile are independent of the inclination angle of the sidewalls of the pattern. Thus, in the embodiment, the length of the shadow is obtained by using these positions as references.

Figure 19:
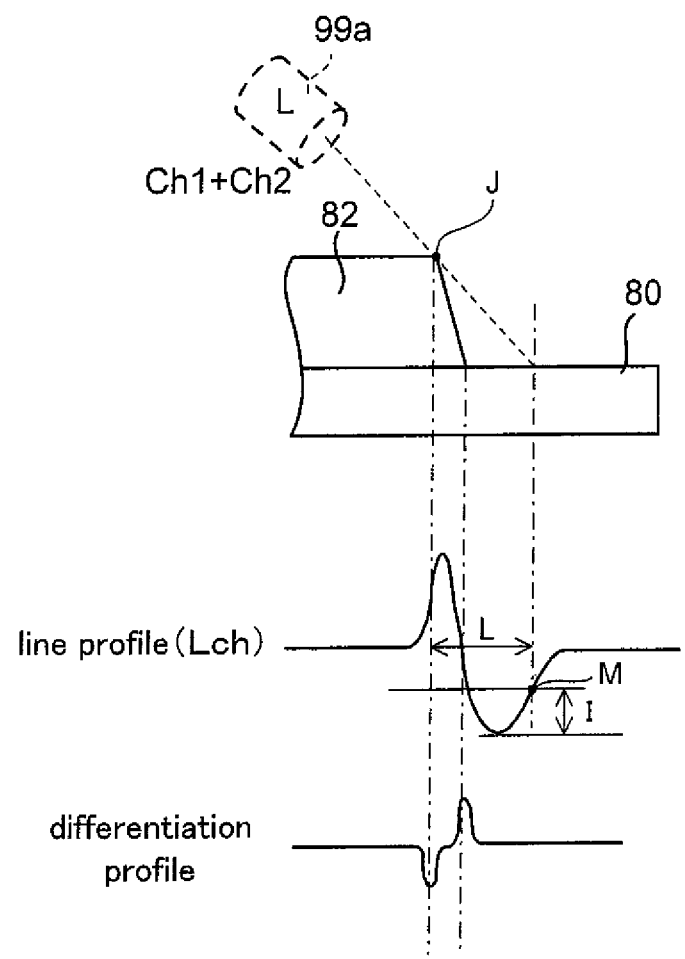
FIG. 19 is a schematic view explaining a method (fourth method) of detecting the length of the shadow in the second embodiment.

FIG. 19 is a schematic view explaining a method (fourth method) of detecting the length of the shadow in the embodiment.

As shown in FIG. 19, in the embodiment, the differentiation profile is obtained and a position J of the upper end of the sidewall of the pattern is detected from the maximum value of the differentiation profile by using the method described with reference to FIG. 18. Note that the position of the lower end of the sidewall may be detected instead of the upper end.

Next, the image processing unit 12 extracts the normalized line profile by the method as described above with referring to FIGS. 6 and 7. Then, the predetermined threshold I is set, and a position M of the one located farther from the pattern of two points where the recess portion of the line profile intersects with the threshold I is detected.

Thereafter, the image processing unit 12 detects the distance between the position M and the position J of the upper end of the sidewall of the pattern as the length L of the shadow, where the position M is the one located farther from the pattern of the two points where the recess portion of the line profile intersects with the threshold I.

The method of the embodiment as described above (hereafter referred to as a fourth method) can prevent the variation in the length of the shadow due to the inclination angle of the sidewall of the pattern, and can measure the height of the pattern in high accuracy even in the case of a sample having a fluctuation in the inclination angle of the sidewall.

EXAMPLE 4

In Example 4, the length of the shadow was detected again by using the fourth method on the basis of the image data acquired in the measurement shown in FIG. 16, and a dependency of the length of the shadow on the inclination angle of the sidewall was examined.

Figure 20:
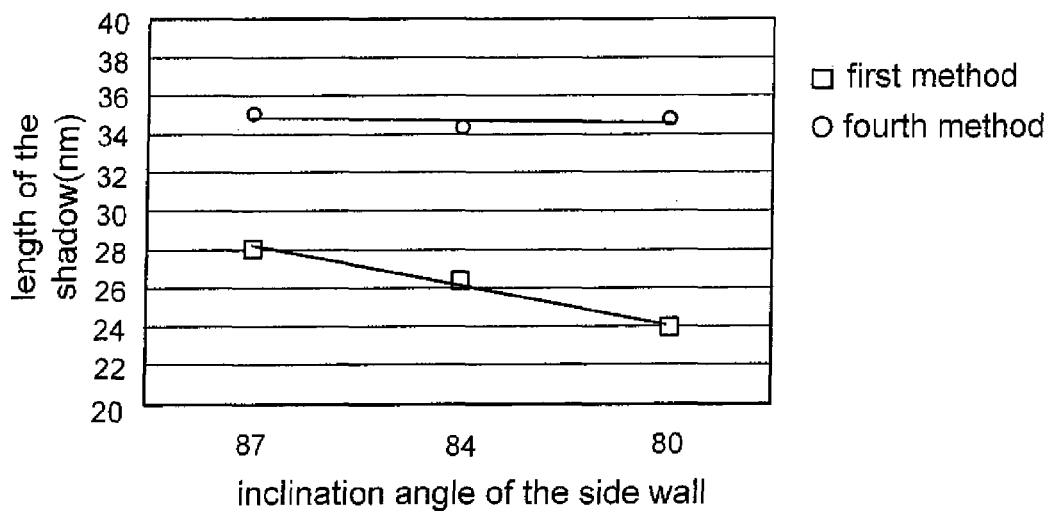
FIG. 20 is a graph showing a relation between the inclination angle of the sidewall of the pattern and the length of the shadow obtained by using each of the first method and the fourth method in Example 4.

FIG. 20 is a graph showing a relation between the inclination angle of the sidewall of the pattern and the length of the shadow obtained by using each of the first method and the fourth method in Example 4.

As shown in FIG. 20, the length of the shadow detected by using the fourth method is longer than that detected by using the first method by about 7 nm. However, it is confirmed that, in the fourth method, the length of the shadow does not change when the inclination angle of the sidewall changes.

EXAMPLE 5

In Example 5, the length of the shadow of each of the first mask 50 and the second mask 60 shown in FIGS. 9A and 9B was detected by using the first method and the fourth method, and a correlation between the measurement result obtained with the AFM and each result of the detection using each of the methods was evaluated.

Figure 21:
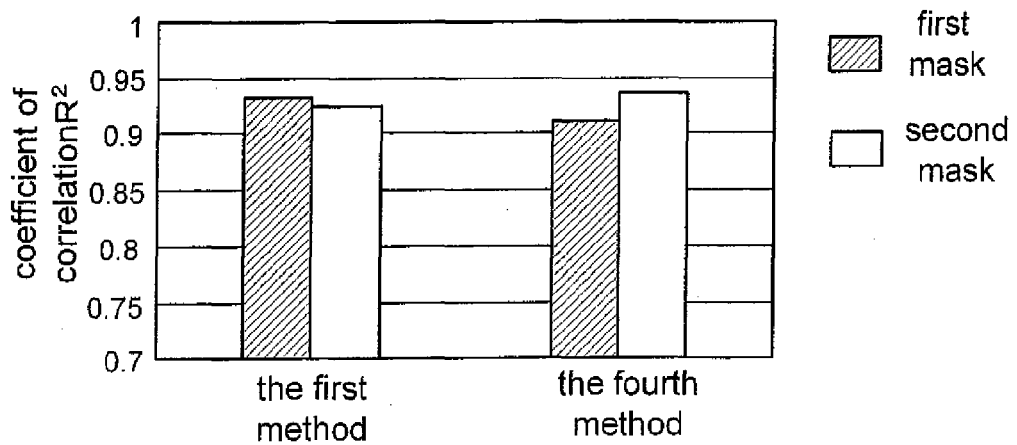
FIG. 21 is a graph showing a coefficient of correlation between the height of the pattern obtained with the AFM and the length of the shadow obtained by using each of the first method and the fourth method in Example 5.

FIG. 21 is a graph showing a coefficient of correlation between the height of the pattern obtained with the AFM and the length of the shadow obtained by using each of the first method and the fourth method in Example 5.

As shown in FIG. 21, a high correlation is confirmed between the measurement result obtained with the AFM and the result of the detection using the fourth method, as similar to the first method.

EXAMPLE 6

In Example 6, the height of the pattern of each of the first mask 50 and the second mask 60 shown in FIGS. 9A and 9B was measured on the basis of the length of the shadow detected by using the fourth method.

First, in Example 6, the apparent angle θ of the detector was measured and was found to be 56.8° for the first mask 50 and to be 55.0° for the second mask 60.

Next, the length of the shadow of each of the first mask 50 and the second mask 60 was detected by using the fourth method, and the height of the pattern was obtained on the basis of the above-described apparent angle θ of the detector.

Figure 22A:
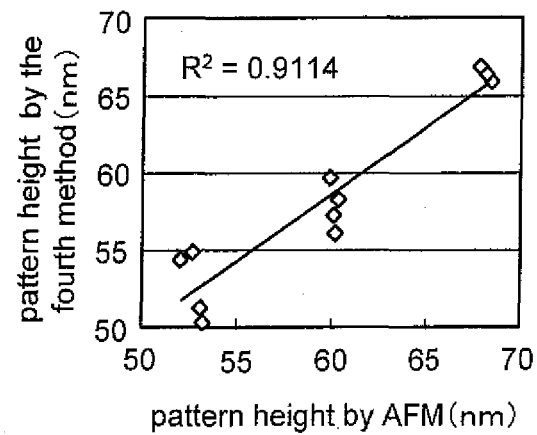
FIGS. 22A and 22B are graphs each showing a correlation between the height of the pattern obtained by using the fourth method on the basis of the length of the shadow and the height of the pattern obtained with the AFM in Example 6.
Figure 22B:
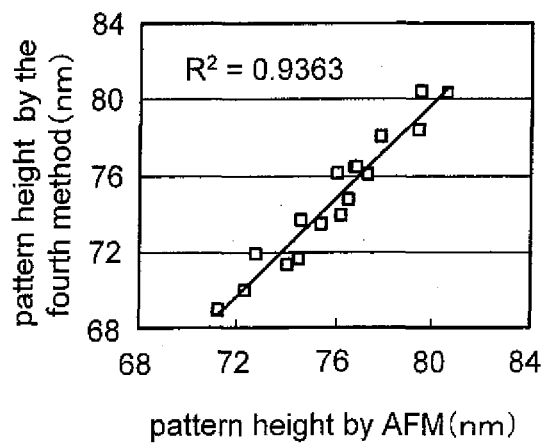

FIG. 22A is a graph showing a correlation between the pattern height of the first mask 50 detected in Example 6 and that measured with the AFM. FIG. 22B is a graph showing a correlation between the pattern height of the second mask 60 detected in Example 6 and that measured with the AFM.

As shown in FIGS. 22A and 22B, it is confirmed that an excellent correlation between the pattern height detected by using the fourth method and the measurement result obtained with the AFM can be obtained for the first mask 50 and the second mask 60.

What is claimed is:

1. A pattern-height measurement method comprising the steps of:
    irradiating a surface of a sample with an electron beam while scanning the electron beam over the surface of the sample, and detecting an intensity of secondary electrons emitted from the surface of the sample by the irradiation of the electron beam using a detector disposed above the surface of the sample;
    generating image data on the basis of a detection signal of the detector, where the image data is obtained by capturing an image of the surface of the sample;
    extracting, by using an image processing unit, intensity distribution of the secondary electrons along a line intersecting with an edge of a pattern formed on the surface of the sample on the basis of the image data, and detecting a length of a shadow of the pattern on the basis of a recess portion of the intensity distribution of the secondary electrons; and
    calculating a height of the pattern on the basis of the length of the shadow.

2. The pattern-height measurement method according to claim 1, wherein
    a plurality of the detectors are arranged around an optical axis of the electron beam, and
    a plurality of pieces of image data are generated on the basis of detection signals from the plurality of detectors, where the plurality of pieces of image data are obtained by capturing images of the surface of the sample in directions different from each other.

3. The pattern-height measurement method according to claim 2, wherein the intensity distribution of the secondary electrons is extracted from the image data taken in a direction orthogonal to the edge of the pattern.

4. The pattern-height measurement method according to claim 1, wherein a distance between two points where the intensity distribution of the secondary electrons near the edge intersects with a predetermined threshold is detected as the length of the shadow.

5. The pattern-height measurement method according to claim 4, wherein the threshold is set within a range higher than a minimum value of a recess portion of a intensity distribution curve of the secondary electrons and lower than an intensity of the secondary electrons in a flat portion adjacent to the recess portion of the intensity distribution curve of the secondary electrons.

6. The pattern-height measurement method according to claim 1, wherein a distance between a minimum value portion of the intensity distribution of the secondary electrons and a point on a side away from the pattern where the intensity distribution of the secondary electrons near the edge intersects with a predetermined threshold is detected as the length of the shadow.

7. The pattern-height measurement method according to claim 1, wherein a square root of an area of a region surrounded by the intensity distribution of the secondary electrons near the edge and a straight line indicating a predetermined threshold is detected as the length of the shadow.

8. The pattern-height measurement method according to claim 1, wherein a distance between one of an upper end and an lower end of the edge of the pattern and a point on a side away from the pattern where the intensity distribution of the secondary electrons near the edge intersects with a predetermined threshold is detected as the length of the shadow.

9. The pattern-height measurement method according to claim 1, wherein the height of the pattern is calculated on the basis of the length of the shadow and an apparent angle of the detector to the surface of the sample.

10. The pattern-height measurement method according to claim 1, wherein the height of the pattern is obtained by adding a predetermined offset value to the length of the shadow, where the offset value is determined by a material of the surface of the sample.

11. A pattern-height measurement apparatus comprising:
    an electron beam scanning unit configured to irradiate a surface of a sample with an electron beam while scanning the electron beam over the surface of the sample;
    a detector disposed above the surface of the sample and configured to detect an intensity of secondary electrons emitted from the surface of the sample by the irradiation of the electron beam;

a signal processing unit configured to generate image data on the basis of a detection signal of the detector, the image data obtained by capturing an image of the surface of the sample;

an image processing unit including a secondary electron intensity distribution extracting means for extracting intensity distribution of the secondary electrons along a line intersecting with an edge of a pattern formed on the surface of the sample on the basis of the image data, and a shadow length detecting means for detecting a length of a shadow of the pattern on the basis of a recess portion of the intensity distribution of the secondary electrons near the edge; and a calculating unit configured to calculate a height of the pattern on the basis of the length of the shadow detected by the image processing unit.

12. The pattern-height measurement apparatus according to claim 11, wherein a plurality of the detectors are arranged around an optical axis of the electron beam.

\* \* \* \* \*